(12) United States Patent
Downing

(10) Patent No.: US 11,832,960 B2
(45) Date of Patent: Dec. 5, 2023

(54) AUTOMATED HEALTH REVIEW SYSTEM

(71) Applicant: Bart M Downing, Hopkinsville, KY (US)

(72) Inventor: Bart M Downing, Hopkinsville, KY (US)

( * ) Notice: Subject to any disclaimer, the term of this patent is extended or adjusted under 35 U.S.C. 154(b) by 273 days.

(21) Appl. No.: 16/900,823

(22) Filed: Jun. 12, 2020

(65) Prior Publication Data

US 2021/0386364 A1 Dec. 16, 2021

(51) Int. Cl.
| | | |
|---|---|---|
| *G16H 10/60* | (2018.01) | |
| *G16H 50/20* | (2018.01) | |
| *A61B 5/00* | (2006.01) | |
| *G16H 50/30* | (2018.01) | |
| *G16H 15/00* | (2018.01) | |
| *G16H 40/20* | (2018.01) | |
| *G16H 50/50* | (2018.01) | |
| *G16H 50/70* | (2018.01) | |
| *G06F 21/62* | (2013.01) | |
| *G16H 70/60* | (2018.01) | |

(52) U.S. Cl.
CPC .............. *A61B 5/48* (2013.01); *A61B 5/7475* (2013.01); *G06F 21/6245* (2013.01); *G16H 10/60* (2018.01); *G16H 15/00* (2018.01); *G16H 40/20* (2018.01); *G16H 50/20* (2018.01); *G16H 50/30* (2018.01); *G16H 50/50* (2018.01); *G16H 50/70* (2018.01); *G16H 70/60* (2018.01)

(58) Field of Classification Search
CPC ....... A61B 5/48; A61B 5/7475; A61B 5/4842; G06F 21/6245; G16H 10/60; G16H 15/00; G16H 40/20; G16H 50/20; G16H 50/30; G16H 50/50; G16H 50/70; G16H 70/60; G16H 70/20
See application file for complete search history.

(56) References Cited

U.S. PATENT DOCUMENTS

| | | |
|---|---|---|
| 5,839,438 A | 11/1998 | Grattinger et al. |
| 6,090,044 A | 7/2000 | Bishop et al. |
| 6,122,351 A | 9/2000 | Schlueter, Jr. et al. |
| 6,475,143 B2 | 11/2002 | Iliff |
| 7,344,496 B2 | 3/2008 | Iliff |
| 7,490,048 B2 | 2/2009 | Joao |
| 8,548,827 B2 | 10/2013 | Gotthardt et al. |
| 8,655,681 B2 | 2/2014 | Friedlander et al. |

(Continued)

*Primary Examiner* — Maroun P Kanaan
(74) *Attorney, Agent, or Firm* — OMNIVAULT LLC; Robert Denis

(57) ABSTRACT

A system and method for providing health care diagnosis, and more specifically, to a system and method for providing automated health condition review and diagnosis with testing recommendations is disclosed. The system includes a condition analyzer server coupled to online prior medical records sources, a current treating facility processor for generating a set of current patient data, the current patient data comprises observations, conditions, vital signs, and complaints, and a data storage device containing one or more sets of one or more predetermined criteria from reference sources and record results. The condition analyzer server return a report containing recommendations potential diagnosis, additional testing recommendations, and reference source materials utilized in generating the potential diagnosis, and additional testing recommendations to the current treating facility.

3 Claims, 9 Drawing Sheets

(56) References Cited

U.S. PATENT DOCUMENTS

| | | |
|---|---|---|
| 8,924,236 B2 | 12/2014 | Marchosky |
| 9,589,231 B2 | 3/2017 | Csurka et al. |
| 2009/0177495 A1* | 7/2009 | Abousy ................ G16H 40/67 |
| | | 705/3 |
| 2019/0164283 A1 | 5/2019 | Kawagishi et al. |
| 2020/0111578 A1* | 4/2020 | Koblick ................ G16H 20/10 |

* cited by examiner

AUTOMATED HEALTH REVIEW SYSTEM

TECHNICAL FIELD

This application relates in general to a system and method for providing health care diagnosis, and more specifically, to a system and method for providing automated health condition review and diagnosis with testing recommendations.

BACKGROUND

When diagnosing patients, healthcare professionals have an overwhelming amount of data in front of them that the human mind cannot manage alone. The number of combinations of diseases/conditions and symptoms is staggering. Therefore, many people are not properly diagnosed until long after their symptoms appear, if they are properly diagnosed at all.

Therefore, a need exists for an automated diagnosis and testing recommendation assistant that accepts all relevant data (demographic, personal, test results, etc.) into a computer system that will run the data against established criteria to highlight to the medical professional what conditions warrant further review. These recommendations may be presented to a treating physician for consideration while diagnostic testing and treatment of a patient occurs.

SUMMARY

In accordance with the present invention, the above and other problems are solved by providing a system and method for an automated health condition review and diagnosis with testing recommendations according to the principles and example embodiments disclosed herein.

In one embodiment, the present invention is a system for providing automated health condition review and diagnosis with testing recommendations. The system includes a condition analyzer server coupled to online prior medical records sources, a current treating facility processor for generating a set of current patient data, the current patient data comprises observations, conditions, vital signs, and complaints, and a data storage device containing one or more sets of one or more predetermined criteria from reference sources and record results. The condition analyzer server return a report containing recommendations potential diagnosis, additional testing recommendations, and reference source materials utilized in generating the potential diagnosis, and additional testing recommendations to the current treating facility.

In another embodiment, the present invention is a method for providing automated health condition review and diagnosis with testing recommendations. The method generates a set of current patient data, the current patient data comprises observations, conditions, vital signs, and complaints at a current treating facility, submits the set of current patient data to a condition analyzer server for processing, parses the set of current patient data to generate prior medical record sources and corresponding online sources, current medical conditions, and current observations, requests copies of the prior medical records from the online sources, receives copies of the prior medical records from the online sources, parses the prior medical records to generate additional prior medical record sources and corresponding online sources, requests copies of the additional prior medical records from the online sources, receives copies of the additional prior medical records from the online sources, compares the set of current patient data, prior medical records, and additional prior medical records with one or more sets of one or more predetermined criteria from reference sources and record results, generates a report containing recommendations potential diagnosis, additional testing recommendations, and reference source materials utilized in generating the potential diagnosis, and additional testing recommendations, and returns the report containing recommendations potential diagnosis, additional testing recommendations, and reference source materials utilized in generating the potential diagnosis, and additional testing recommendations current treating facility.

The foregoing has outlined rather broadly the features and technical advantages of the present invention in order that the detailed description of the invention that follows may be better understood. Additional features and advantages of the invention will be described hereinafter that form the subject of the claims of the invention.

It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only, and is not intended as a definition of the limits of the present invention.

BRIEF DESCRIPTION OF THE DRAWINGS

Referring now to the drawings in which like reference numbers represent corresponding parts throughout.

DETAILED DESCRIPTION

Figure 1:
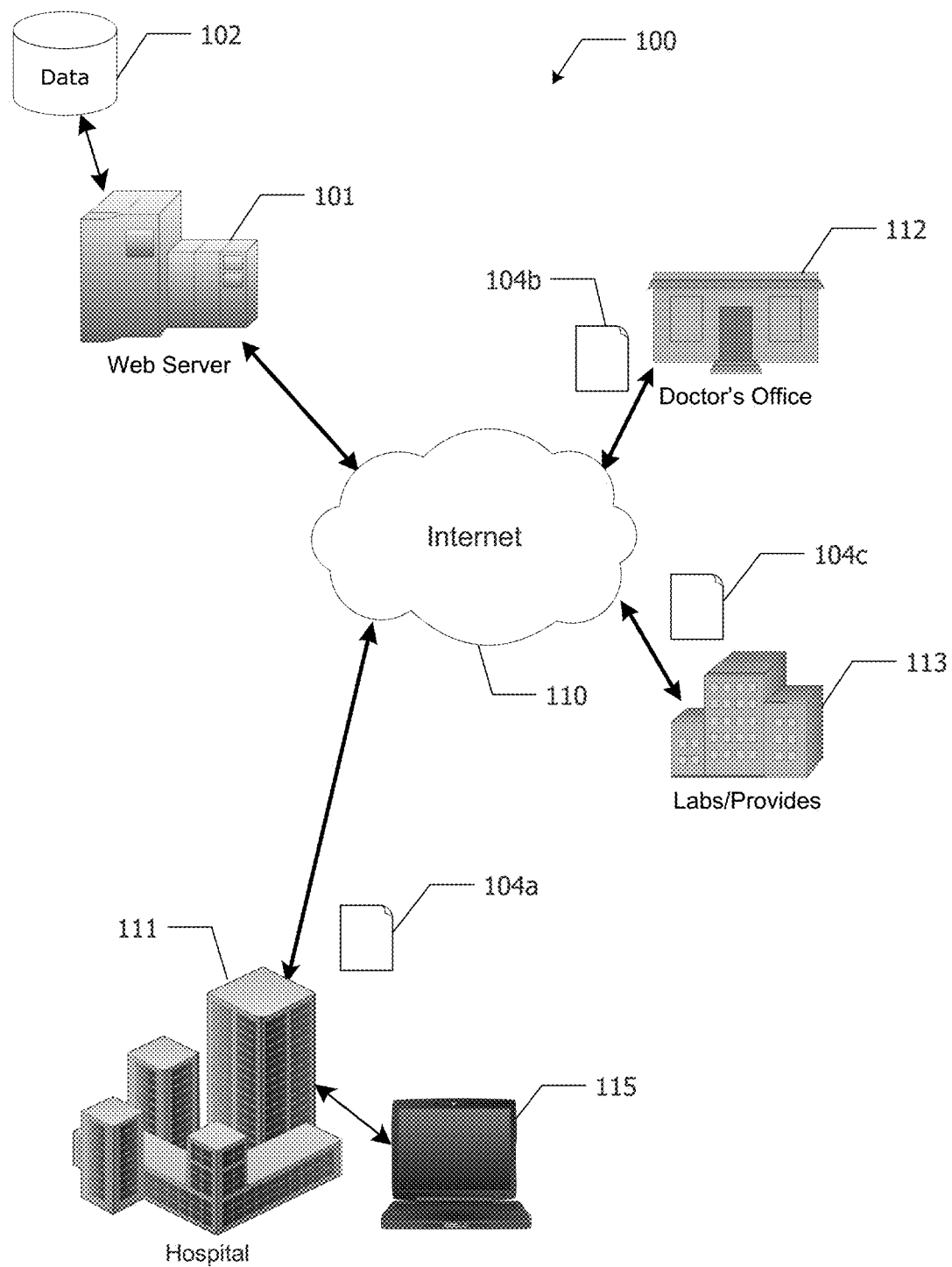
FIG. 1 illustrates an example embodiment for a system that provides automated health condition review and diagnosis with testing recommendations according to the present invention.

This application relates in general to a system and method for providing health care diagnosis, and more specifically, to a system and method for providing automated health condition review and diagnosis with testing recommendations according to the present invention.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

In describing embodiments of the present invention, the following terminology will be used. The singular forms "a," "an," and "the" include plural referents unless the context clearly dictates otherwise. Thus, for example, reference to "a needle" includes reference to one or more of such needles and "etching" includes one or more of such steps. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. As used herein, the singular forms "a," "an," and "the" are intended to include the plural forms as well, unless the context clearly indicates otherwise.

It further will be understood that the terms "comprises," "comprising," "includes," and "including" specify the presence of stated features, steps or components, but do not preclude the presence or addition of one or more other features, steps or components. It also should be noted that in some alternative implementations, the functions and acts noted may occur out of the order noted in the figures. For example, two figures shown in succession may in fact be executed substantially concurrently or may sometimes be executed in the reverse order, depending upon the functionality and acts involved.

As used herein, the term "about" means that dimensions, sizes, formulations, parameters, shapes, and other quantities and characteristics are not and need not be exact, but may be approximated and/or larger or smaller, as desired, reflecting tolerances, conversion factors, rounding off, measurement error and the like, and other factors known to those of skill. Further, unless otherwise stated, the term "about" shall expressly include "exactly," consistent with the discussion above regarding ranges and numerical data.

The term "mobile application" refers to an application executing on a mobile device such as a smartphone, tablet, and/or web browser on any computing device.

The terms "patient," "healthcare provider," "healthcare professional" and "user" refer to an entity, e.g. a human, using the Automated Health Checking System including any software or smart device application(s) associated with the invention. The term user herein refers to one or more users.

The term "connection" refers to connecting any component as defined below by any means, including but not limited to, a wired connection(s) using any type of wire or cable for example, including but not limited to, coaxial cable(s), fiberoptic cable(s), and ethernet cable(s) or wireless connection(s) using any type of frequency/frequencies or radio wave(s). Some examples are included below in this application.

The term "invention" or "present invention" refers to the invention being applied for via the patent application with the title "Automated Health Review System." Invention may be used interchangeably with healthcare system.

In general, the present disclosure relates a system and method for providing health care review and diagnosis with testing recommendations. To better understand the present invention, FIG. 1 illustrates an example embodiment for a system that provides automated health condition review and diagnosis with testing recommendations according to the present invention.

Doctors have an overwhelming amount of data in front of them that the human mind cannot manage alone. Often the data points to potential issues, but there is too much data for the healthcare provider to sift through in search of the most likely diagnosis. The number of combinations of diseases/conditions and symptoms is staggering. Therefore, many people are not properly diagnosed until long after their symptoms appear, if they are properly diagnosed at all. The solution to this information overload is to enter all relevant data (demographic, personal, test results, etc.) into a computer system that will run the data against established criteria to highlight to the healthcare professional what conditions warrant further review.

The system concept would operate as follows: examples of common data collected by a healthcare professional are entered into a medical records system. Information related to observed conditions, personal demographics, allergies, observations of mitral valve prolapse, patient's height/weight, evidence of Irritable Bowel Syndrome, hypertension, race or ethnicity, diabetes, sleep apnea, history of depression, and other related observations would be documented and entered into the medical records system at a medical center 111.

Evidence of similar prior conditions may be searched in available medical records 104a-c from other healthcare providers 112 and laboratories 113 who previously treated a patient. All of this information may be sent to and processed by a system 100 on a remote web server 101. All of the collected data may be processed and compiled in a manner 105 that is useful for treating professionals to consider when recommending additional testing and treatment options for a patient.

While many independent tools may exist, no overarching tool that screens all patients visiting a primary healthcare facility is currently available and in use. A tool 101 such as the one identified here would find more conditions requiring early and routine intervention. Over the long run, the early intervention would lower healthcare costs for both patient and provider.

The invention may use any type of network such as a single network, multiple networks of a same type, or multiple networks of different types which may include one or more of a direct connection between devices, including but not limited to a local area network (LAN), a wide area network (WAN) (for example, the Internet), a metropolitan area network (MAN), a wireless network (for example, a general packet radio service (GPRS) network), a long term evolution (LTE) network, a telephone network (for example, a Public Switched Telephone Network or a cellular network), a subset of the Internet, an ad hoc network, a fiber optic network (for example, a fiber optic service (often known as FiOS) network), or any combination of the above networks.

Smart devices mentioned herein the present application may also use one or more sensors to receive or send signals, such as wireless signals like, Bluetooth™, wireless fidelity, infrared, Wi-Fi, and LTE. Any smart device mentioned in this application may be connected to any other component or smart device via wired communications (e.g., conductive wire, coaxial cable, fiber optic cable, ethernet cable, twisted pair cable, transmission line, waveguide, etc.) or a combination of wired and wireless communications. The invention's method and/or system may use a single server device or a collection of multiple server devices and/or computer systems.

The system and method described above may be implemented in many different forms of applications, software, firmware, and hardware. The actual software or smart device application codes or specialized control software, hardware or smart device application(s) used to implement the invention's systems and methods is not limiting of the implementation. Thus, the operation and behavior of the systems and methods were described without reference to the specific software or firmware code. Software, smart device application(s), firmware, and control hardware can be designed to implement the systems and methods based on the description herein.

While all of the above functions are described to be provided to users via a mobile application on a smartphone, one of ordinary skill will recognize that any computing device including tablets, laptops, and general purpose computing devices may be used as well. In at least one embodiment, all of the services described herein are provided using web pages being accessed from a web server 201 using a web browser such as Safari™, Firefox™, Chrome™ Duck-DuckGo™, and the like. All of the screen examples described herein show user interface elements that provide the functionality of the present invention. The arrangement, organization, presentation, and use of particular user input/output (I/O) elements including hyperlinks, buttons, text fields, scrolling lists, and similar I/O elements are shown herein for example embodiments only to more easily convey the features of the present invention. The scope of the present invention should not be interpreted as being limited by any of these elements unless expressly recited within the attached claims.

For the purposes of the example embodiment of FIG. 1, various functions are shown to be performed on different programmable computing devices that communicate with each other over the Internet 110. These computing devices may include smartphones 101a, laptop computers 101b, tablets (not shown), and similar devices so long as the disclosed functionality of the mobile application described herein is supported by the particular computing device. One of ordinary skill will recognize that this functionality is grouped as shown in the embodiment for clarity of description. Two or more of the processing functions may be combined onto a single processing machine. Additionally, it may be possible to move a subset of processing from one of the processing systems shown here and retain the functionality of the present invention. The attached claims recite any required combination of functionality onto a single machine, if required, and all example embodiments are for descriptive purposes.

For all of the above devices that are in communication with each other, some or all of them need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects, and in order to more fully illustrate one or more aspects. Similarly, although process steps, method steps, algorithms or the like may be described in a sequential order, such processes, methods, and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method or algorithm is carried out or executed. Some steps may be omitted in some aspect or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example, an end-user computer system, a client computer, a network server or other server system, a mobile computing device (e.g., tablet computing device, mobile phone, smartphone, laptop or other appropriate computing device), a consumer electronic device, a music player or any other suitable electronic device, router, switch or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines or other appropriate virtual environments).

Figure 2A:
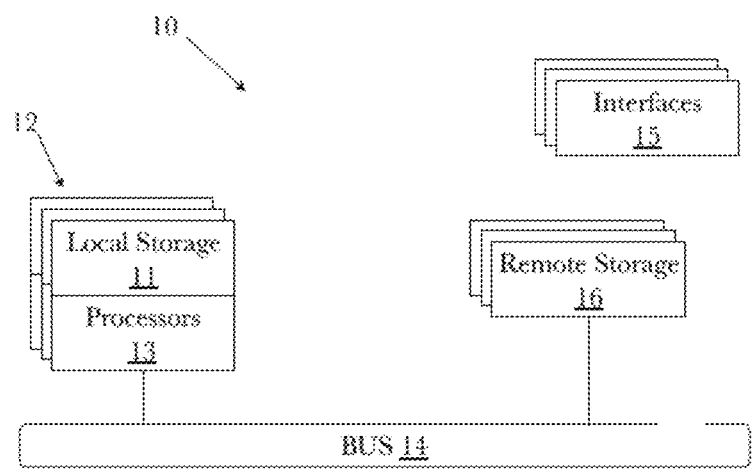
FIG. 2a is a block diagram illustrating an exemplary hardware architecture of a computing device.

Referring now to FIG. 2a, there is a block diagram depicting an exemplary computing device 10 suitable for implementing at least a portion of the features or functionalities disclosed herein. A computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network, a metropolitan area network, a local area network, a wireless network, the Internet or any other network, using known protocols for such communication, whether wireless or wired.

In one aspect, a computing device 10 includes one or more central processing units (CPU) 12, one or more interfaces 15, and one or more buses 14 (such as a peripheral component interconnect (PCI) bus). When acting under the control of appropriate software or firmware, a CPU 12 may be responsible for implementing specific functions associated with the functions of a specifically configured computing device or machine. For example, in at least one aspect, a computing device 10 may be configured or designed to function as a server system utilizing a CPU 12, local memory 11 and/or remote memory 16, and interface(s) 15. In at least one aspect, a CPU 12 may be caused to perform one or more of the different types of functions and/or operations under the control of software modules or components, which for example, may include an operating system and any appropriate applications software, drivers, and the like.

A CPU 12 may include one or more processors 13 such as for example, a processor from one of the Intel, ARM, Qualcomm, and AMD families of microprocessors. In some aspect, processors 13 may include specially designed hardware such as application-specific integrated circuits (ASICs), electrically erasable programmable read-only memories (EEPROMs), field-programmable gate arrays (FPGAs), and so forth, for controlling operations of a computing device 10. In a particular aspect, a local memory 11 (such as non-volatile random access memory (RAM) and/or read-only memory (ROM), including for example, one or more levels of cached memory) may also form part of a CPU 12. However, there are many different ways in which memory may be coupled to a system 10. Memory 11 may be used for a variety of purposes such as, for example, caching and/or storing data, programming instructions, and the like. It should be further appreciated that a CPU 12 may be one of a variety of system-on-a-chip-(SOC) type hardware that may include additional hardware such as memory or graphics processing chips, such as a QUALCOMM SNAPDRAGON™ or SAMSUNG EXYNOS™ CPU as are becoming increasingly common in the art for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may, for example, support other peripherals used with a computing device 10. Among the interfaces that may be provided are ethernet interfaces, frame relay interfaces, cable interfaces, DSL interfaces, token ring interfaces, graphics interfaces, and the like. In addition, various types of interfaces may be provided such as, for example, universal serial bus (USB), serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast ethernet interfaces, gigabit ethernet interfaces, serial ATA (SATA) or external SATA (ESATA) interfaces, high-definition multimedia interfaces (HDMI), digital visual interfaces (DVI), analog or digital audio interfaces, asynchronous transfer mode (ATM) interfaces, high-speed serial interfaces (HSSI), point of sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 2a illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and a server system (such as a server system described in more detail below).

Regardless of network device configuration, the system of an aspect may employ one or more memories or memory modules (for example, remote memory block 16 and local memory 11) configured to store data, program instructions for the general-purpose network operations or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information or any other specific or generic non-program information described herein.

Because such information and program instructions may be employed to implement one or more systems or methods described herein, at least some network device aspects may include non-transitory machine-readable storage media, which, for example, may be configured or designed to store program instructions, state information, and the like for performing various operations described herein. Examples of such non-transitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device) or they may be removable such as swappable flash memory modules (such as "thumb drives" or other removable media designed for rapidly exchanging physical storage devices), "hot-swappable" hard disk drives or solid state drives, removable optical storage disks, or other such removable media, and that such integral and removable storage media may be utilized interchangeably. Examples of program instructions include both object code, such as may be produced by a compiler, machine code, such as may be produced by an assembler or a linker, byte code, such as may be generated by for example by a JAVA™ compiler and may be executed using a JAVA™ virtual machine or equivalent, or files containing higher level code that may be executed by the computer using an interpreter (for example, scripts written in Python™, Perl™, Ruby™, Groovy™, or any other scripting language).

Figure 2B:
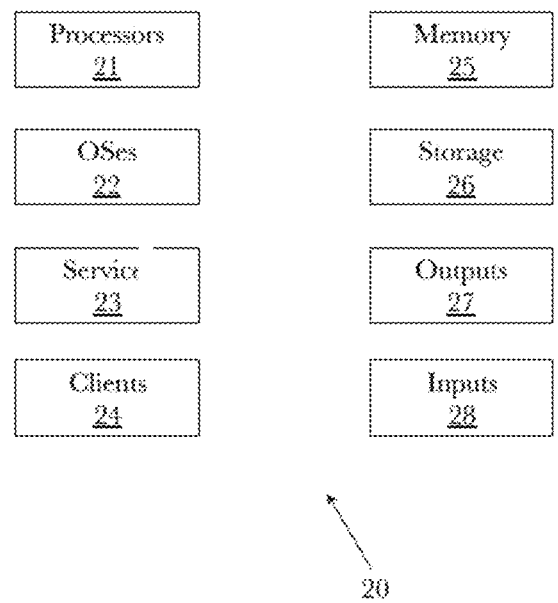
FIG. 2b is a block diagram illustrating an exemplary logical architecture for a client device.

In some aspects, systems may be implemented on a standalone computing system. Referring now to FIG. 2b, there is a block diagram depicting a typical exemplary architecture of one or more aspects or components thereof on a standalone computing system. A computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the LINUX™ operating system, ANDROID™ operating system, and the like. In many cases, one or more shared services 23 may be operable in system 20, and may be useful for providing common services to client applications 24. Services 23 may, for example, be WINDOWS™ services, user-space common services in a LINUX™ environment or any other type of common service architecture used with an operating system 21. Input devices 28 may be of any type suitable for receiving user input including, for example, a keyboard, touchscreen, microphone (for example, for voice input), mouse, touchpad, trackball or any combination thereof. Output devices 27 may be of any type suitable for providing output to one or more users, whether remote or local to system 20, and may include, for example, one or more screens for visual output, speakers, printers or any combination thereof. Memory 25 may be RAM having any structure and architecture known in the art for use by processors 21, for example to run software. Storage devices 26 may be any magnetic, optical, mechanical, memristor or electrical storage device for storage of data in digital form (such as those described above, referring to FIG. 2a). Examples of storage devices 26 include flash memory, magnetic hard drive, CD-ROM, and the like.

Figure 2C:
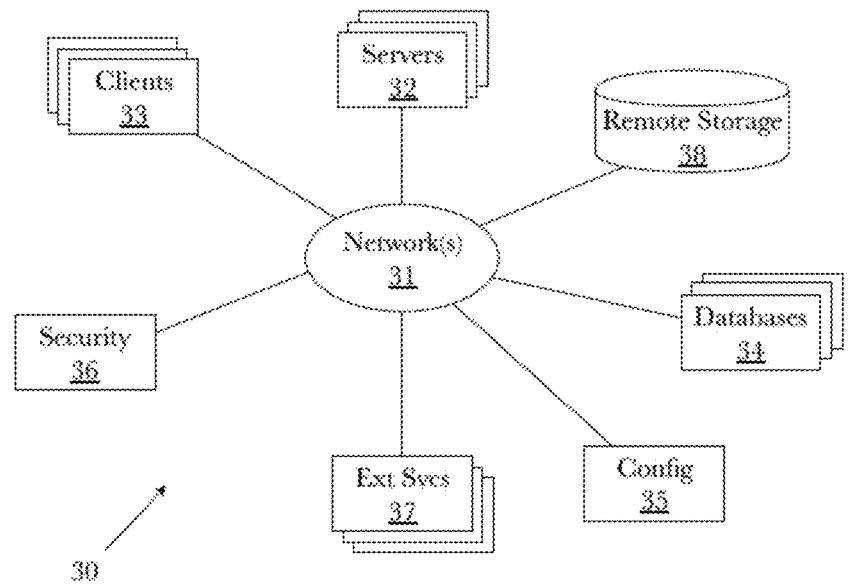
FIG. 2c is a block diagram showing an exemplary architectural arrangement of clients, servers, and external services.

In some aspects, systems may be implemented on a distributed computing network, such as one having any number of clients and/or servers. Referring now to FIG. 2c, there is a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 2b. In addition, any number of servers 32 may be provided for handling requests received from one or more clients 33. Clients 33 and servers 32 may communicate with one another via one or more electronic networks 31, which may be in various aspects any Internet, wide area network, mobile telephony network (such as CDMA or GSM cellular networks), wireless network (such as WiFi, WiMAX, LTE, and so forth) or local area network (or indeed any network topology known in the art; the aspect does not prefer any one network topology over another). Networks 31 may be implemented using any known network protocols, including, for example, wired and/or wireless protocols.

In addition, in some aspects, servers 32 may call external services 37 when needed to obtain additional information or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored on a server system 32 in the Cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and use a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system or a logical database within an overall database management system. Unless a specific meaning is specified for a given use of the term "database," it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web system. It should be understood by one having ordinary skill in the art that any configuration or security subsystems known in the art now or in the future may be used in conjunction with aspects without limitation, unless a specific security 36 or configuration system or approach is required by the description of any specific aspect.

Figure 2D:
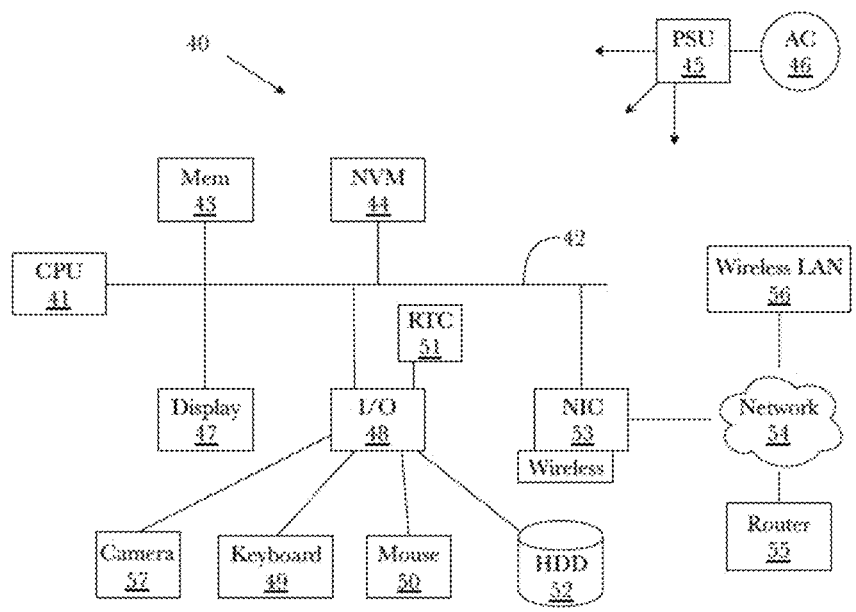
FIG. 2d is another block diagram illustrating an exemplary hardware architecture of a computing device.

FIG. 2d shows an exemplary overview of a computer system 40 as may be used in any of the various locations throughout the system. It is exemplary of any computer that may execute code to process data. Various modifications and changes may be made to a computer system 40 without departing from the broader scope of the system and method disclosed herein. A CPU 41 is connected to a bus 42, to which the bus is also connected to memory 43, nonvolatile memory 44, display 47, I/O unit 48, and network interface card (NIC) 53. An I/O unit 48 may typically be connected to peripherals such as a keyboard 49, pointing device 50, hard disk 52, real-time clock 51, camera 57, and other peripheral devices. A NIC 53 connects to a network 54, which may be the Internet or a local network, which local network may or may not have connections to the Internet. The system may be connected to other computing devices through the network via a router 55, wireless local area network 56 or any other network connection. Also shown as part of a system 40 is a power supply unit 45 connected, in this example, to a main alternating current (AC) supply 46. Not shown are batteries that could be present and many other devices and modifications that are well known, but are not applicable to, the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles or other integrated hardware devices).

In various aspects, functionality for implementing systems or methods of various aspects may be distributed among any number of client and/or server components. For example, various software modules may be implemented for performing various functions in connection with the system of any particular aspect, and such modules may be implemented to run on server and/or client components.

Figure 3:
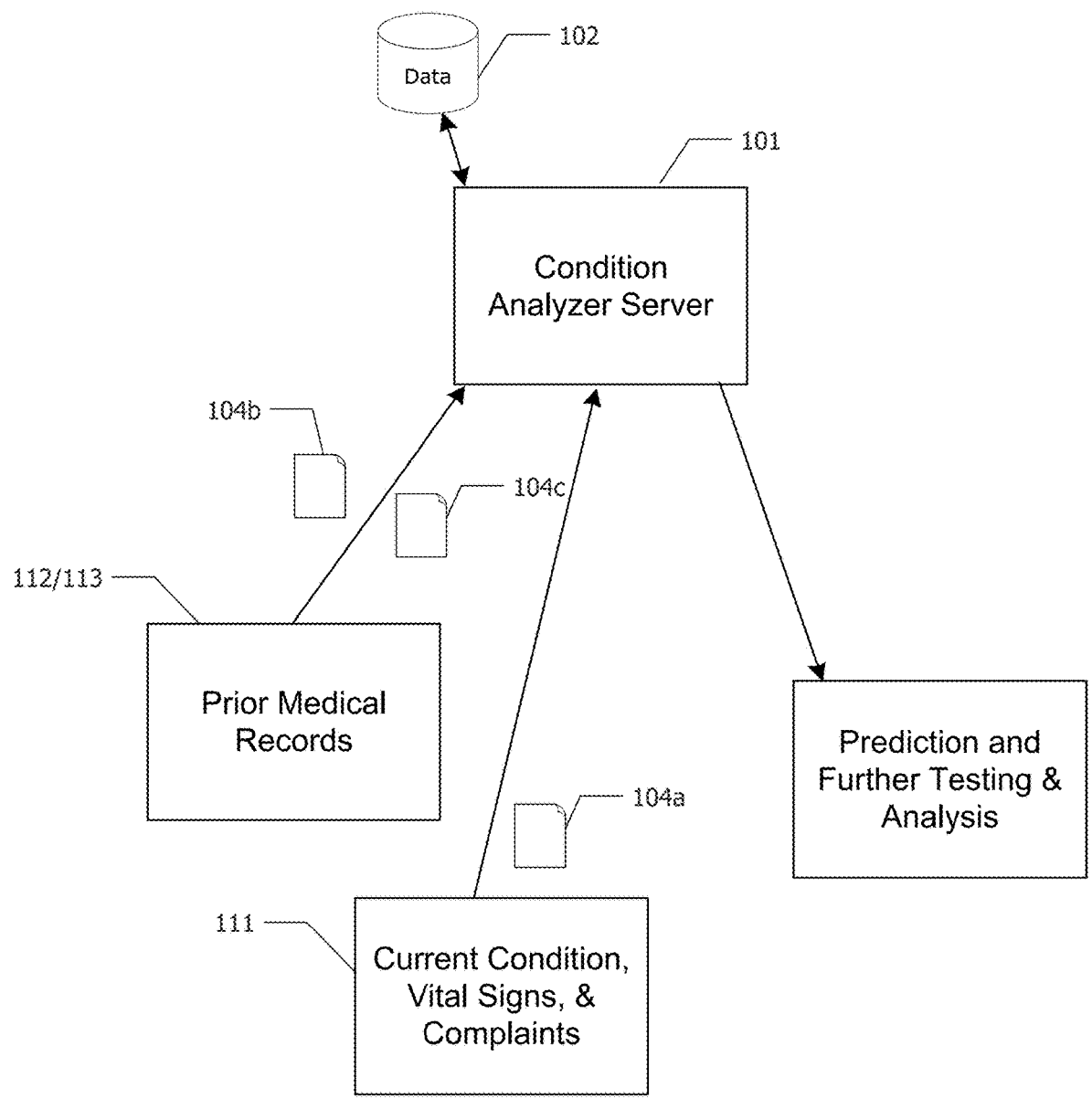
FIG. 3 illustrates another example embodiment of a system for providing automated health condition review and diagnosis with testing recommendations according to the present invention.

FIG. 3 illustrates another example embodiment of a system for providing automated health condition review and diagnosis with testing recommendations according to the present invention. The system 100 comprises a condition analyzer server 101 that receives prior medical records 104b-c from various healthcare providers 112/113 along with a set of current observations, conditions, vital signs, and complaints 104a from a current treating facility 111 for processing. All of the data is analyzed against a library of known medical symptoms and conditions 102 to form a set of potential diagnoses and further testing options 105 that are returned to the current treating facility 111 for consideration and possible use. The set of potential diagnoses and further testing options 105 may be automatically generated once a patient enters a facility and an initial triage, medical history, and vital signs are obtained. The set of potential diagnoses and further testing options 105 may be reviewed by a treating physician at an initial stage of examination and diagnosis to assist the physician at the beginning of treatment. Automating the process to occur without human interaction ensures that the set of potential diagnoses and further testing options 105 will be obtained and made available for all patient situations.

Figure 4:
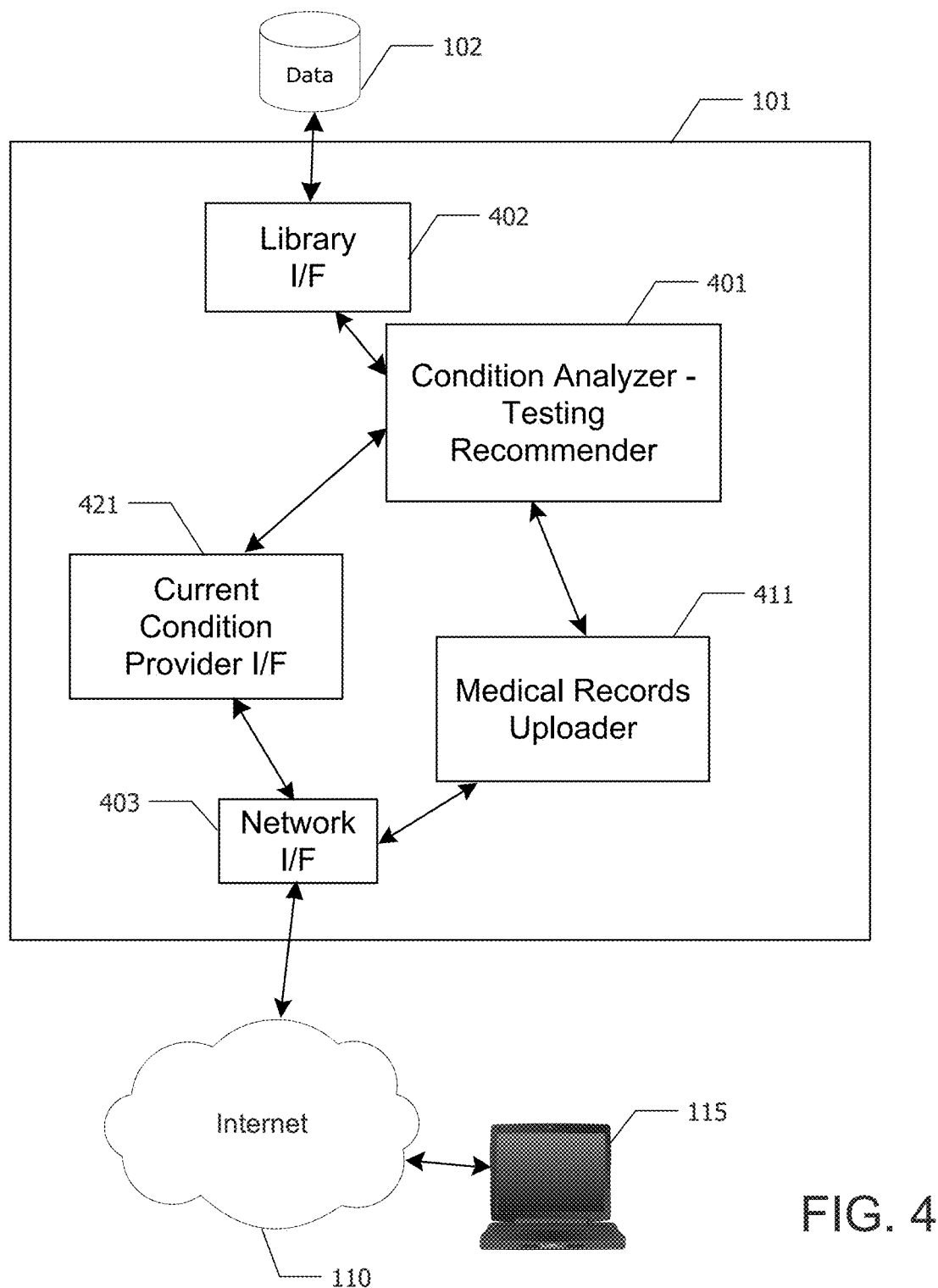
FIG. 4 illustrates a computing system of software components providing automated health condition review and diagnosis with testing recommendations according to the present invention.

FIG. 4 illustrates a computing system of software components providing automated health condition review and diagnosis with testing recommendations according to the present invention. The remote web server 101 generates the set of potential diagnoses and further testing options 105 using processing elements that include a condition analyzer-testing recommender 401, a medical library interface 402 coupled to a library of known medical symptoms and conditions 102, a network interface 403, a medical records uploader 411, and a current condition provider interface 421. The remote web server 101 is accessed by healthcare professionals and healthcare facilities using a local computing system 115 over the Internet 110.

Figure 5A:
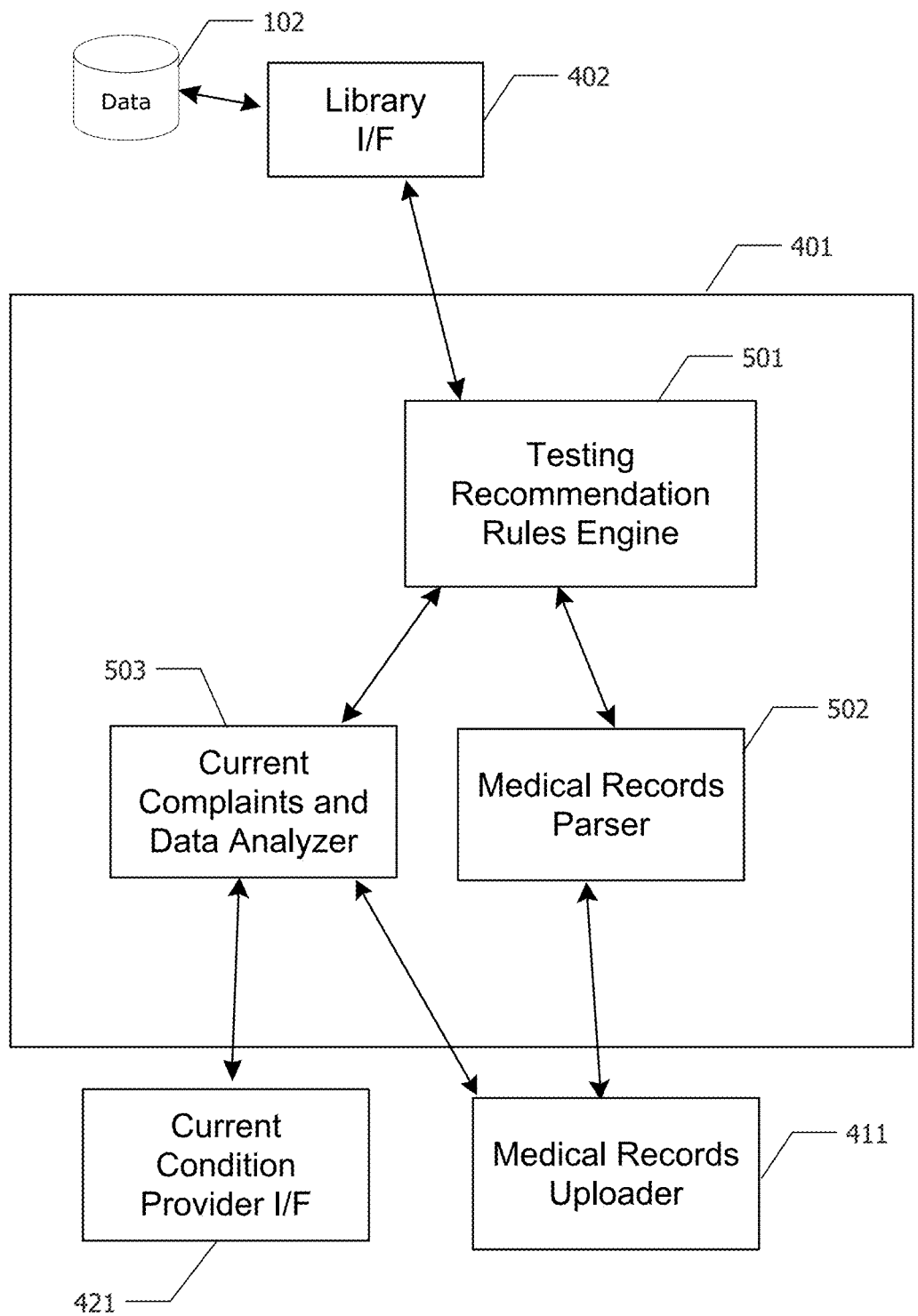
FIGS. 5a-c illustrate a detailed embodiment of a computing system of software components providing automated health condition review and diagnosis with testing recommendations according to the present invention.

The condition analyzer-testing recommender 401, which is described in more detail in reference to FIG. 5a, processes all of the received patient data to analyze it against a library of known medical symptoms and conditions 102 to form the set of potential diagnoses and further testing options 105 that are returned 111 for consideration and possible use. The set of potential diagnoses and further testing options 105 may be automatically generated once a patient enters a facility and an initial triage, medical history, and vital signs are entered into the web server 101.

The medical library interface 402 coupled to the library of known medical symptoms and conditions 102 permits the condition analyzer-testing recommender 401 to access the library of known medical symptoms and conditions 102 based upon the data received from the treating physician. The library 102 may be routinely updated with the latest medical studies, treatment regimens, and related data as it becomes available. This automated updating of the library provides treating physicians with the most current information available.

The network interface 403 connects the web server 101 to the Internet 110 to send and receive communication from physicians and healthcare providers. The network interface 403 performs all necessary data formatting, data packet creation, data encryption for security, and data transmission and reception when the web server 101 communicates with other processing systems disclosed herein. The network interface 403 is also responsible for ensuring reception of any communications to other computing systems and to log any errors or attempts to hack into any medical data stores.

Figure 5B:
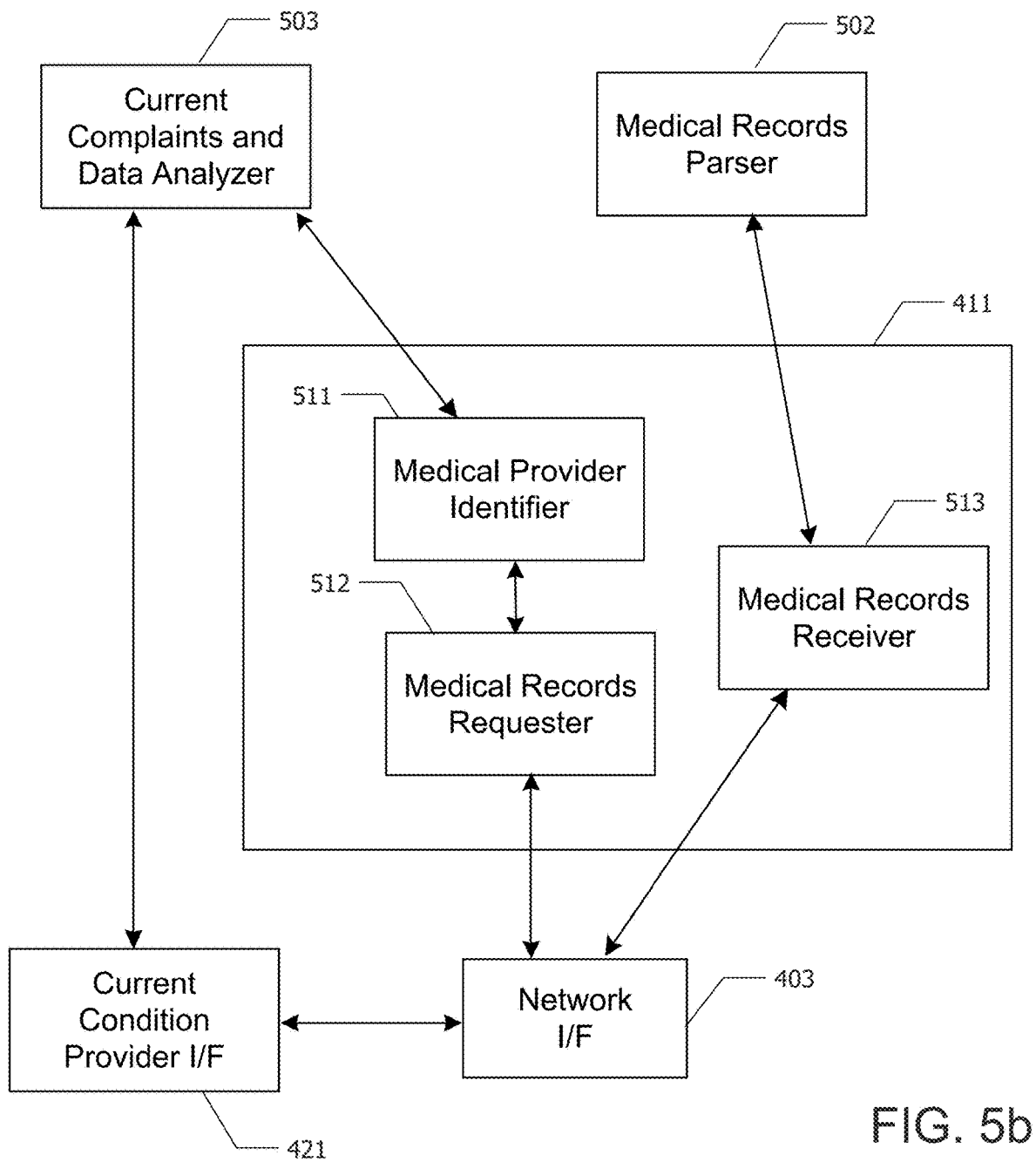

The medical records uploader 411, which is described in more detail below in reference to FIG. 5b, is provided information from the condition analyzer-testing recommender 401 regarding the identity of any prior healthcare providers who may have medical records available regarding the patient. The medical records uploader 411 is responsible for obtaining authorization to obtain the patient's medical records from each provider, for submitting the proper request for records electronically, and for uploading all medical records made available to the system 100. All of these obtained records are then provided to the condition analyzer-testing recommender 401 for use in analyzing the patient's condition and providing possible diagnoses and further testing recommendations.

Figure 5C:
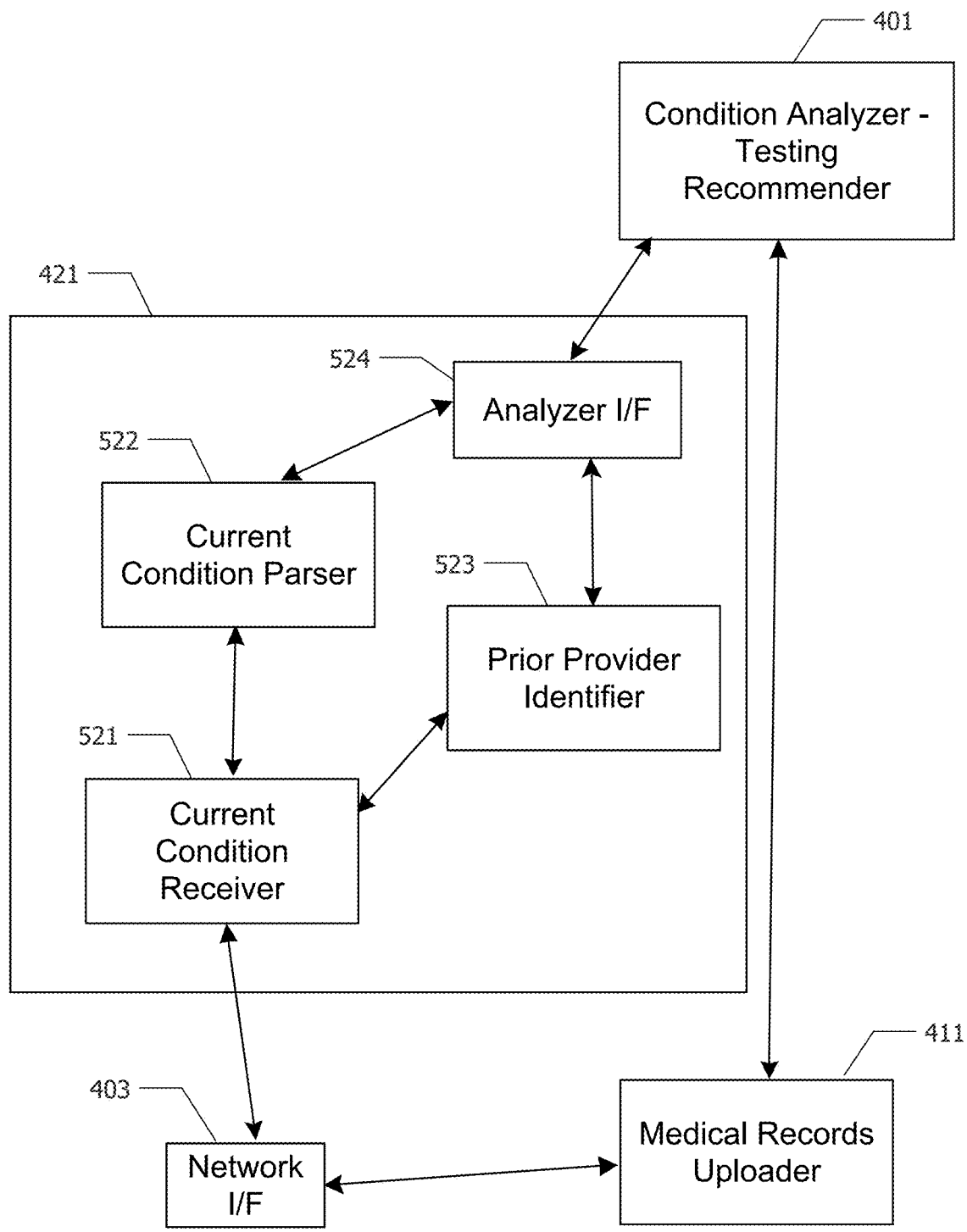

The current condition provider interface 421, which is described in more detail below in reference to FIG. 5c, provides an interface for a treating physician and his/her healthcare facility to send the set of current observations, conditions, vital signs, and complaints 104a from a current treating facility 111 for processing. The current condition provider interface 421 may permit the treating physician and his/her healthcare facility to send updated data and additional requests for analysis and recommendations when additional data warrants further analysis. The treating physician and his/her healthcare facility may also provide identity data of additional sources of prior medical records for use in an updated analysis. The treating physician and his/her healthcare facility 111 interacts with the web server 101 via this interface 421.

FIGS. 5a-c illustrate a detailed embodiment of a computing system of software components providing automated health condition review and diagnosis with testing recommendations according to the present invention. FIG. 5a illustrates the components of the condition analyzer-testing recommender 401 as it interacts with other processing elements within the remote web server 101. The condition analyzer-testing recommender 401 comprises a testing recommendation rules engine 501, a medical records parser 502, and a current complaint and data analyzer 503.

The testing recommendation rules engine 501 processes all of the past and current medical data regarding the patient to determine possible diagnoses and recommended testing and treatment options. The medical records parser 502 receives the prior medical records from the medical records uploader 411 and parses them into individual relevant facts that may be used by the testing recommendation rules engine 501 as is generates its possible diagnoses and recommended testing and treatment options. The medical records parser 502 may be provided a set of search conditions by the testing recommendation rules engine 501 to locate relevant facts, conditions, and test results that may be useful to the testing recommendation rules engine 501.

The current complaint and data analyzer 503 obtains the prior medical records from the medical records uploader 411 and parses them into individual relevant facts that may be used by the testing recommendation rules engine 501 as is generates its possible diagnoses and recommended testing and treatment options. The current complaint and data analyzer 503 uses the set of current observations, conditions, vital signs, and complaints 104a from a current treating facility 111 to provide data useful to the testing recommendation rules engine 501 for its processing.

FIG. 5b illustrates the components of the medical records uploader 411 as it interacts with other processing elements within the remote web server 101. The medical records uploader 411 comprises a medical provider identifier 511, a medical records requester 512, and a medical records receiver 513. These processing elements interact to obtain prior medical records for the patient and provide them to the condition analyzer-testing recommender 401 for use.

The medical provider identifier 511 receives possible prior healthcare providers and related facilities found in the set of current observations, conditions, vital signs, and complaints 104a from a current treating facility 111 and begins the process to request and receive these prior medical records. The medical provider identifier 511 also analyzes any of the prior medical records to identify additional healthcare providers and related facilities who have provided treatment and testing of the patient. The medical provider identifier 511 continues to seek any prior medical records of the patient that may be useful to the analysis. This request for medical records may be iterative and continue throughout the analysis process.

The medical records requester 512 generates a request to all identified healthcare providers for access to and electronic copies of all available medical records of the patient. The medical records requester 512 is responsible for obtaining all required records authorizations from the current healthcare facility and treating physician while complying with medical record privacy regulations.

The medical records receiver 513 receives electronic copies of all prior medical records available for the patient for use in the generation of possible diagnoses and potential additional testing recommendations. The electronic copies of all prior medical records available for the patient may be used within the testing recommendation rules engine 501 as needed.

FIG. 5c illustrates the components of the current condition provider interface 421 as it interacts with other processing elements within the remote web server 101. The current condition provider interface 421 comprises a current condition data receiver 521, a current condition data parser 522, a prior provider identifier 523, and an analyzer interface 524. These processing elements interact to obtain current condition data for the patient and provide them to the condition analyzer-testing recommender 401 for use.

The current condition data receiver 521 receives the set of current observations, conditions, vital signs, and complaints 104a from a current treating facility 111 for use in the generation of possible diagnoses and potential additional testing recommendations. The set of current observations, conditions, vital signs, and complaints 104a from a current treating facility 111 may be used within the current condition provider interface 421 as needed.

The current condition data parser 522 receives the set of current observations, conditions, vital signs, and complaints 104a from a current treating facility 111 from the current condition data receiver 521 and parses it into data useful in additional processing. The current condition data parser 522 may be provided a set of search conditions by the testing recommendation rules engine 501 to locate relevant facts, conditions, and test results that may be useful to the testing recommendation rules engine 501.

The prior provider identifier 523 identifies possible prior healthcare providers and related facilities that have provided testing and treatment to the patient. The identity of these possible prior healthcare providers and related facilities may be used to obtain prior medical records.

The analyzer interface 524 provides a common data communications interface for the current condition data receiver 521 to send data to and receive data from the condition analyzer-testing recommender 401.

Figure 6:
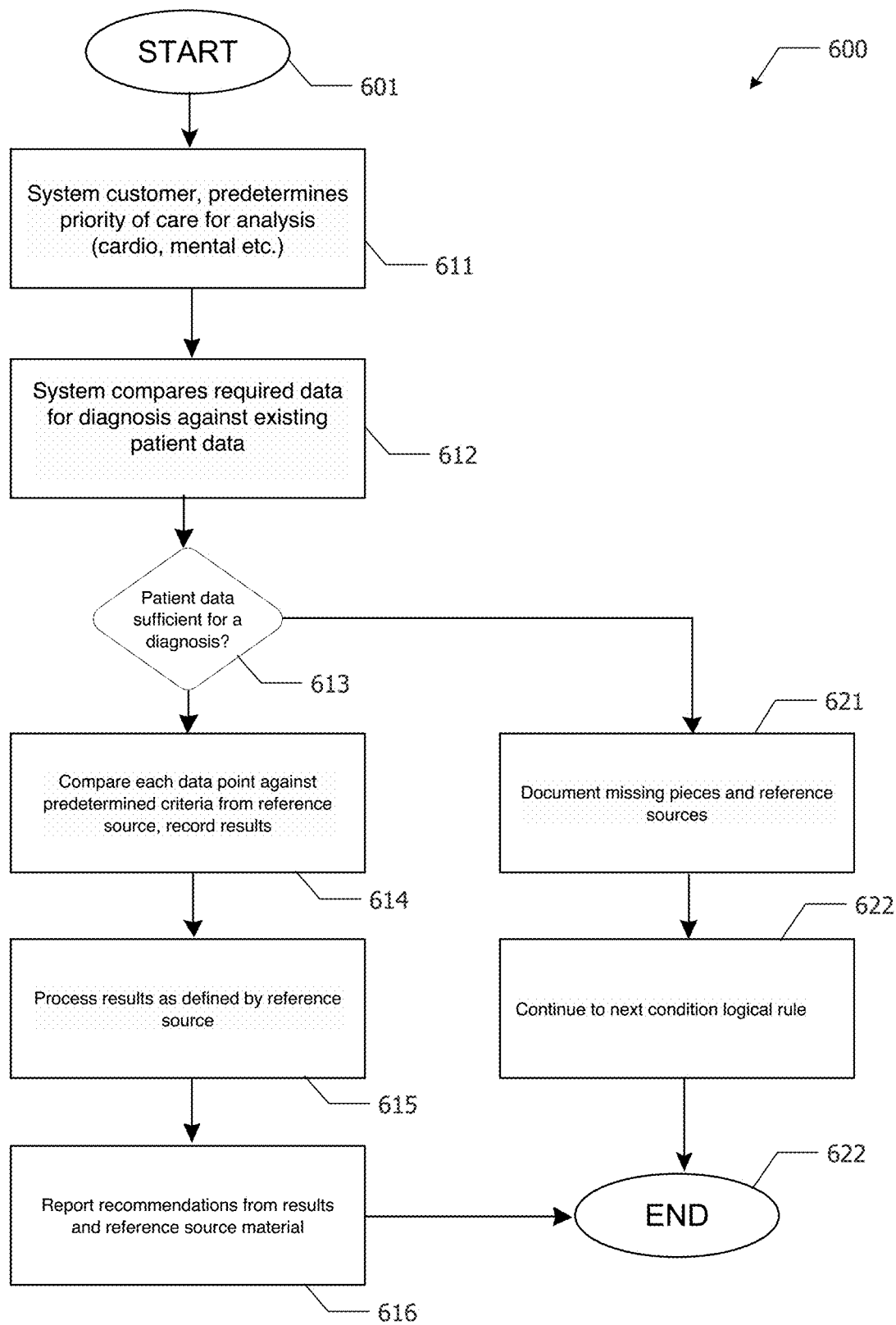
FIG. 6 illustrates a flowchart corresponding to a method performed by software components providing automated health condition review and diagnosis with testing recommendations according to the present invention.

FIG. 6 illustrates a flowchart corresponding to a method performed by software components providing automated health condition review and diagnosis with testing recommendations according to the present invention. The process 600 begins 601 when step 611 predetermines a system customer priority of care for analysis, such as cardio, mental etc.

In step 612, the system compares required data for diagnosis against existing patient data. Test step 613 determines whether required data available for analysis is sufficient for determining a diagnosis against existing patient data, and if so step 614 compares each data point against a set of one or more predetermined criteria from reference sources and record results. Any found results are processed in step 615 as defined in the reference source. Step 616 reports recommendations and corresponding referenced source material in step 616 to the treating physician before the process ends 602.

When test step 613 determines that there is insufficient data to generate a diagnosis, step 621 documents missing data and corresponding references sources. Step 622 processes the next logical rule from a set of rules in a rules engine. When all of the rules have been processed, the process ends 620.

The embodiments described herein are implemented as logical operations performed by a computer. The logical operations of these various embodiments of the present invention are implemented (1) as a sequence of computer-implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Even though particular combinations of features are recited in the present application, these combinations are not intended to limit the disclosure of the invention. In fact, many of these features may be combined in ways not specifically recited in this application. In other words, any of the features mentioned in this application may be included to this new invention in any combination or combinations to allow the functionality required for the desired operations.

No element, act, or instruction used in the present application should be construed as critical or essential to the invention unless explicitly described as such. Further, the phrase "based on" is intended to mean "based, at least in part, on" unless explicitly stated otherwise. The phrase "connected to a billboard" means any component or smart device that is capable to connect to a billboard or billboards by any means wired and/or wireless, regardless if a server or server(s) or computer system(s) is required in any step of the connection process. Any singular term used in this present patent application is applicable to its plural form even if the singular form of any term is used.

In the present application, all or any part of the invention's software or application(s) or smart device application(s) may be installed on any of the user's or operator's smart device(s), any server(s) or computer system(s) or web application(s) required to allow communication, control, and transfer of content(s) or data between any combination of the components.

What is claimed:

1. A system for providing automated health condition review and diagnosis with testing recommendations, the system comprising:

a current treating facility processor for generating a set of current patient data, the current patient data comprises observations, conditions, vital signs, and complaints;

a data storage device containing one or more sets of one or more predetermined criteria from reference sources and record results;

a condition analyzer server coupled to online prior medical records sources, wherein the condition analyzer server comprises:

a current condition provider interface for providing an interface for a treating physician at the current treating facility to send the set of current observations, conditions, vital signs, and complaints for processing, wherein the current condition provider interface comprises:

a testing and diagnosis recommendation rules engine for analyzing the prior medical records and current patient data to determine possible diagnoses and recommended testing and treatment options;

a medical records parser for generating individual relevant facts that may be used by the testing recommendation rules engine to generate possible diagnoses and recommended testing and treatment options from the prior medical records from the medical records uploader;

a current complaints and data analyzer for generating a second set of individual relevant facts that may be used by the testing recommendation rules engine to generate possible diagnoses and recommended testing and treatment options from the prior medical records from the medical records uploader; and a medical records uploader for obtaining authorization to obtain the patient's medical records from each provider, for submitting the proper request for records electronically, and for uploading all medical records made available to the system;

a condition analyzer-testing recommender for analyzing the current patient data against a library of known medical symptoms and conditions to form the one or more sets of one or more predetermined criteria from reference sources and record results; and a medical library interface coupled to the data storage device for providing access to the one or more sets of one or more predetermined criteria from reference sources and record results;

wherein the condition analyzer server return a report containing recommendations potential diagnosis, additional testing recommendations, and reference source materials utilized in generating the potential diagnosis, and additional testing recommendations to the current treating facility.

2. The system according to claim 1, wherein the medical records uploader comprises:

a medical provider identifier for analyzing the prior medical records to identify additional healthcare providers and related facilities who have provided treatment and testing of the patient from possible prior healthcare providers online sources found in the set of current patient data;
a medical records requestor for generating a request to all identified healthcare providers for access to and electronic copies of all available medical records of the patient; and
a medical records receiver for receiving electronic copies of all prior medical records available for the patient for use in the generation of possible diagnoses and potential additional testing recommendations.

3. The system according to claim 1, wherein the condition analyzer-testing recommender comprises:
a current condition receiver for receiving the set of current observations, conditions, vital signs, and complaints from a current treating facility for use in the generation of possible diagnoses and potential additional testing recommendations;
a current condition parser for parsing the set of current observations, conditions, vital signs, and complaints from the current treating facility into data useful in additional processing;
a prior provider identifier for identifying possible prior healthcare providers and related online medical record that have provided testing and treatment to the patient; and
an analyzer interface for communicating with the current condition data receiver to send data to and receive data from the condition analyzer-testing recommender.

\* \* \* \* \*